United States Patent [19]
Ghetie et al.

[11] Patent Number: 5,578,706
[45] Date of Patent: Nov. 26, 1996

[54] METHODS AND COMPOSITIONS CONCERNING HOMOGENOUS IMMUNOTOXIN PREPARATIONS

[75] Inventors: Victor F. Ghetie; Jonathan W. Uhr; Ellen S. Vitetta, all of Dallas, Tex.

[73] Assignee: Board of Regents, The University of Texas, Austin, Tex.

[21] Appl. No.: 147,768

[22] Filed: Nov. 4, 1993

[51] Int. Cl.$^6$ .................................................. C07K 16/46
[52] U.S. Cl. .................. 530/391.7; 530/391.1; 424/178.1; 424/183.1
[58] Field of Search .............. 530/391.1, 391.7; 424/178.1, 183.1

[56] References Cited

U.S. PATENT DOCUMENTS

| | | | |
|---|---|---|---|
| 4,340,535 | 7/1982 | Voisin et al. | 530/391.9 |
| 5,106,951 | 4/1992 | Morgan et al. | 530/391.9 |

OTHER PUBLICATIONS

Amlot et al., "A Phase I Study of an Anti–CD22–Deglycosylated Ricin A Chain Immunotoxin in the Treatment of B–Cell Lymphomas Resistant to Conventional Therapy," Blood, 82(9):2624–2633, 1993.

Ghetie et al., "Large scale preparation of an immunoconjugate constructed with human recombinant CD4 and deglycosylated ricin A chain," Journal of Immunological Method, 126 (1990) 135–141.

Masuho et al., "Importance of the Antigen–Binding Valency and the Nature of the Cross–Linking Bond in Ricin A–Chain Conjugates with Antibody," J. Biochem., 91:1583–1591, 1982.

Lord et al., Adv. Drug Delivery Rev, vol. 2, pp. 297–318 (1988).

Vidal et al., Int J Cancer, vol. 36, pp. 705–711 (1985).

Borrebaeck, Journal of Immunological Methods. vol. 123, pp. 157–165 (1989).

Harris et al., TIBTECH, vol. 11, pp. 42–44 (1993).

Hermentin et al., Behring Inst. Mitt, No. 82 pp. 197–215 (1988).

Seaver, Genetic Engineering News (Aug. 1994).

Ghetie et al., J. Immunol. Methods, vol. 112, pp. 267–277 (1988).

Ghetie et al., J. Immunol. Methods, vol. 142, pp. 223–230 (1991).

Marsh et al., Biochemistry, vol. 25, pp. 4461–4467 (1986).

Ghetie et al., Journal of Immunological Methods, vol. 166, pp. 117–122 (1993).

Primary Examiner—Toni R. Scheiner
Attorney, Agent, or Firm—Arnold White & Durkee

[57] ABSTRACT

Immunotoxin preparations are described in which the preparations are enriched for a single species of immunotoxin. Also described are methods for the preparation of the substantially purified immunotoxins (ITs). Also disclosed are methods for determining the most effective species of immunotoxin conjugates for treated diseases and pharmaceutical preparations for such treatments.

8 Claims, 4 Drawing Sheets

METHODS AND COMPOSITIONS CONCERNING HOMOGENOUS IMMUNOTOXIN PREPARATIONS

The government owns rights in the present invention pursuant to grant numbers CA-28149 and CA-41081 from the National Institutes of Health.

BACKGROUND OF THE INVENTION

1. Field of the Invention

The present invention relates generally to the field of immunotoxins, i.e., toxins conjugated to targeting molecules, and to methods for their preparation and use. The invention particularly concerns novel methods of purifying immunotoxins and determining the most effective species of immunotoxin conjugates for treatment of specific diseases.

2. Description of the Related Art

Ricin A chain (RTA) is the catalytic subunit of the plant toxin ricin and is frequently used for the construction of immunotoxins (ITs) (Lord et al., 1988). To be pharmacologically active, RTA-Its must have a disulfide bond between the antibody and the RTA (Masuho et al., 1982). The chemical linkage of RTA to antibody involves the introduction of activated thiol groups into the molecule of antibody and the reaction of the thiolated antibody with reduced RTA. The free thiol groups of the RTA molecule displace the pyridyl disulfide from the activated thiol groups of the antibody to form disulfide linkages. The resulting IT is then purified to remove the free RTA and antibody by two successive chromatographic steps on Blue-SEPHAROSE SEPHACRYL S-200 (Ghetie et al., 1988a; 1991).

Unfortunately, the IT that results from such methods is not a homogeneous product, but contains mixtures of conjugates comprising several molecular species with one, two or more RTAs linked to each molecule of antibody. These mixtures are not easily separated, particularly during scale-up, because their MWs and electrical charges are similar.

This formation of mixtures of conjugates that contain different proportions of deglycosylated A chain (dgA) or other toxin is the principal problem in the preparation of ITs by chemical methods. The mixture usually comprises a major component containing equimolar amounts of antibody and toxin and several other conjugates with two or more toxin molecules per molecule of antibody. This heterogeneity results from the introduction of various numbers of thiol groups per molecule of antibody. Due to the nature of the chemical reaction between the N-succinimidyl group of the crosslinker and the primary amino groups of the antibody, populations of antibody molecules substituted with none, one, two, three and even more than three thiol groups are obtained.

For example, it was reported that when the crosslinker N-succinimidyl-oxycarbonyl-α-methyl-(2-pyridyl-dithio)-toluene (SMPT) was added to the molecule of antibody (mouse $IgG_1$) in a 5-fold molar excess, the average number of thiol (MPT groups) introduced was 2 (Ghetie et al., 1991). However, when the $IgG_1$-MPT was chromatographed through an activated thiol-AGAROSE column in the inventors' laboratory, 25% of the protein did not bind and after treatment with dithiothreitol, it did not release pyridine-2-thione, demonstrating that 25% of the $IgG_1$ molecules were not substituted. This indicated that the average number of MPT groups introduced was 2.7 and not 2. Further, when this thiolated antibody was reacted with dgA, the main component (50%) contained one molecule of dgA per molecule of antibody. This suggested that not all MPT groups introduced into the $IgG_1$ molecule are able to bind dgA and therefore, that the IT may contain some molecules of antibody with unreduced MPT groups.

To decrease the number of MPT groups introduced into the molecule of antibody, a lower molar ratio between SMPT and $IgG_1$ was used (2–3). In this case, the degree of substitution averaged 1 MPT group per molecule of $IgG_1$ and a 180 kDa IT was formed after reacting with dgA. However, the yield of IT obtained (10–15%) was considerably lower than the yield obtained when an $IgG_1$-MPT with 2 MPTs per molecule of $IgG_1$ was used (50–60%) (Ghetie et al., 1991). Therefore, merely adjusting the molar ratio between SMPT and $IgG_1$ is not an efficient way to produce ITs of a particular toxin to antibody molar ratio.

This inability to produce pure antibodies of a particular toxin/antibody ratio has also made it difficult to assess which immunotoxin preparation would be the most beneficial in a pharmacological preparation. Although a comparison of two ITs constructed with either one or two molecules of intact ricin (A+B chains) has been reported (Marsh and Neville, 1986), this comparison has not been done with the ricin A chain conjugated to an antibody. Therefore, there exists an immediate need for a procedure for large scale, efficient preparation of immunotoxins which can be separated according to the toxin/antibody molar ratio.

SUMMARY OF THE INVENTION

The present invention seeks to overcome these and other drawbacks inherent in the prior art by providing efficient procedures for the large scale preparation of immunotoxins for use in various embodiments, such as, for example, in the treatment of cancer and retroviral diseases. The invention also provides novel immunotoxin preparations which are enriched for specific immunotoxin species comprising an antibody molecule conjugated to one, two or three toxin chains, respectively.

As used herein, the term "species" of immunotoxin refers to an immunotoxin of a particular, defined toxin/antibody ratio. For example, an immunotoxin of a single toxin chain conjugated to a single antibody molecule is a separate species from an immunotoxin of two toxin chains conjugated to a single antibody molecule. The terms "enriched" and "substantially purified" are used herein interchangeably. These terms are used to refer to immunotoxin preparations in which a single immunotoxin species is present as a larger proportion of the total immunotoxin in a preparation than in the heterologous conjugation reaction mix.

In certain embodiments, an immunotoxin which has a toxin to antibody ratio of one toxin chain to one antibody molecule ($dgA_1$/IgG), is enriched for that species such that from about 50% to more than about 95% by weight of the total immunotoxin present in the preparation is $dgA_1$/IgG. While it is understood that any preparation containing more than about 50% of that species is within the scope of the present claimed invention, preparations of more than 60% or preparations of more than 80% and even preparations of about 95% of the total immunotoxin being the $dgA_1$/IgG species are also encompassed within the present claimed invention. In other embodiments, an immunotoxin which has a toxin to antibody ratio of two toxin chains to one antibody molecule ($dgA_2$/IgG), is enriched for that species such that from about 30% to about 92% by weight of the total immunotoxin present in the preparation is $dgA_2$/IgG. While it is understood that any preparation containing more than about 30% of that species is within the scope of the present claimed invention, preparations of more than 50% or preparations of more than 70% or even preparations of about 92% by weight of the total immunotoxin is the dgA$_2$/IgG species are also encompassed within the scope of the present claimed invention. In other embodiments, an immunotoxin which has a toxin to antibody ratio of three toxin chains to one antibody molecule (dgA$_3$/IgG), is enriched for that species such that from about 19% to about 81% by weight of the total immunotoxin present in the preparation is dgA$_3$/IgG. While it is understood that any preparation containing more than about 19% of that species is within the scope of the present claimed invention, preparations in which more than 30%, or preparations in which more than 60% or even preparations in which about 81% by weight of the total immunotoxin is the dgA$_2$/IgG species are also encompassed within the scope of the present claimed invention.

As used herein, the term "immunotoxin (IT)" is used to refer to a cytotoxic agent that comprises a cell-binding moiety otherwise described as a "targeting agent" and a toxin moiety linked via a chemical cross-linker, natural peptide, disulfide bond or any other suitable means. The targeting agent or moiety can be an antibody or a fragment thereof, such as a Fab' or Fab fragment, a growth factor, or a hormone that binds selectively to certain cell types. Most often, the targeting agent will be an antibody or a fragment thereof, and preferably will be a monoclonal antibody such as a mouse or human monoclonal antibody or so-called humanized antibody constructs which are known in the art. In certain embodiments, the invention is exemplified by the use of mouse IgG$_1$ as the targeting agent.

The targeting agent is also conjugated to a toxin moiety. The toxin moiety of the immunotoxin may be any one of a variety of toxins that are commonly employed in the art. It may be an intact toxin, a toxin A chain, or a naturally occurring single-chain ribosome-inactivating protein (RIP). Toxins which are encompassed by the invention include, for example, diphtheria toxin (DT) and DT(CRM-45); pseudomonas endotoxin (PE) and PE40; ricin and abrin and blocked forms of both of these; gelonin and saporin. Preferred toxins are contemplated to be those involving ricin, such as ricin A chain, and most preferably, deglycosylated ricin A chain.

The heterologous mixture of immunotoxins is obtained by crosslinking the toxin and antibody molecules by any appropriate method. A preferred method of crosslinking is by using SMPT (N-succinimidyl-oxycarbonyl-α-methyl-(2-pyridyldithio) toluene). The unreacted toxin chains, antibody molecules and small particles are then removed by chromatography and filtration, for example, or by a combination of methods. These methods separate molecules based on the differences in molecular size or in molecular charge at certain pH and ionic strength conditions. These methods are well known in the art and preferred methods include affinity chromatography over activated dye/agarose beds and gel filtration through acrylamide beads, for example. The heterologous mixture is then purified or enriched for the individual immunotoxin species by any of the available separation methods which include, but are not limited to adsorption, partition, ion-exchange or molecular sieve chromatography, electrophoresis, or a combination of such methods. Preferred methods are affinity chromatography over an agarose/dye column and gel filtration.

A certain embodiment of the present invention is a method of purifying immunotoxin preparations. In particular, the purification methods of the invention include obtaining and purifying a heterologous mixture of ITs with different molar ratios of toxin/antibody and then enriching the immunotoxin preparations for a single immunotoxin species. In preferred embodiments, the immunotoxin species is an antibody crosslinked to one, two or three toxin molecules. The antibody is preferably a monoclonal antibody and most preferred is a mouse monoclonal antibody. The preferred toxin is ricin A and more preferred is a deglycolsylated ricin A chain.

Another embodiment of the present invention is a method of obtaining enriched immunotoxin preparations comprising the steps of chemically crosslinking toxin molecules to antibodies to obtain immunotoxin conjugates, removing free toxins and antibodies and separating the individual immunotoxin species. The immunotoxin species may be separated by affinity chromatography and exclusion chromatography, or gel filtration. In certain embodiments, the immunotoxin species may be separated by electrophoresis, preferably SDS-polyacrylamide gel electrophoresis.

Another embodiment of the present invention concerns compositions of immunotoxins of known toxin/antibody molar ratio obtainable by the methods disclosed herein, i.e., immunotoxin preparations and pharmaceutical formulations obtainable by subjecting a heterologous mixture of immunotoxin conjugates to separation methods such as affinity chromatography and gel filtration. Most preferred immunotoxins are those with toxin/Ab ratios of one, two or three.

In certain embodiments the invention concerns pharmaceutical preparations comprising a substantially purified immunotoxin in combination with a pharmacologically acceptable carrier. For certain clinical uses, ITs with two molecules of toxin conjugated to one antibody molecule may be preferred.

The invention also provides methods for introducing immunotoxins into animals, including human subjects, and methods for treating various conditions and diseases, including cancers and lymphomas. These methods generally comprise administering to an animal an effective amount of a pharmaceutically acceptable immunotoxin composition comprising a substantially purified immunotoxin prepared as disclosed herein, in combination with a pharmacologically acceptable carrier. The formulations may be administered parenterally, such as via intravenous, intramuscular or sub-cutaneous injection and the like and are preferably administered parenterally and most preferably are administered intravenously.

It is understood that the preparations of the present invention will have wide utility as compositions for use against a variety of diseases such as cancer and retroviral infections including human immunodeficiency virus (HIV). Also, for the first time, the toxicity, immunogenicity and effectiveness of particular dgA/IgG immunotoxins can be assessed to determine the best molar ratio to be used in pharmacological preparations. It is also understood that in addition to the clinical applications of the preparations of the present invention, the methods of preparation present a new and efficient method of large scale preparation and purification of immunotoxins for clinical, pharmaceutical and various other scientific applications.

BRIEF DESCRIPTION OF THE DRAWINGS

FIG. 1 is a single gel which contains of lanes A–H. Lane A contains IgG$_1$ (RFB4). Lane B contains RFB4-SMPT-dgA; (percentage of bands: 1st=50%, 2nd=30%, 3rd=10%, 4th and 5th=

10%). Lane C contains dgA. Lane D contains high MW markers. Lane E contains low MW markers. Lane F contains reduced IgG$_1$ (RFB4). Lane G contains reduced RFB4-SMPT-dgA. Lane H contains reduced dgA. The molecular weight markers are indicated as follows: 1 is 30 kDa; 2 is 43 kDa; 3 is 67 kDa; 4 is 94 kDa; 5 is 150 kDa; 6 is 170 kDa and 7 is 212 kDa.

Figure 2:
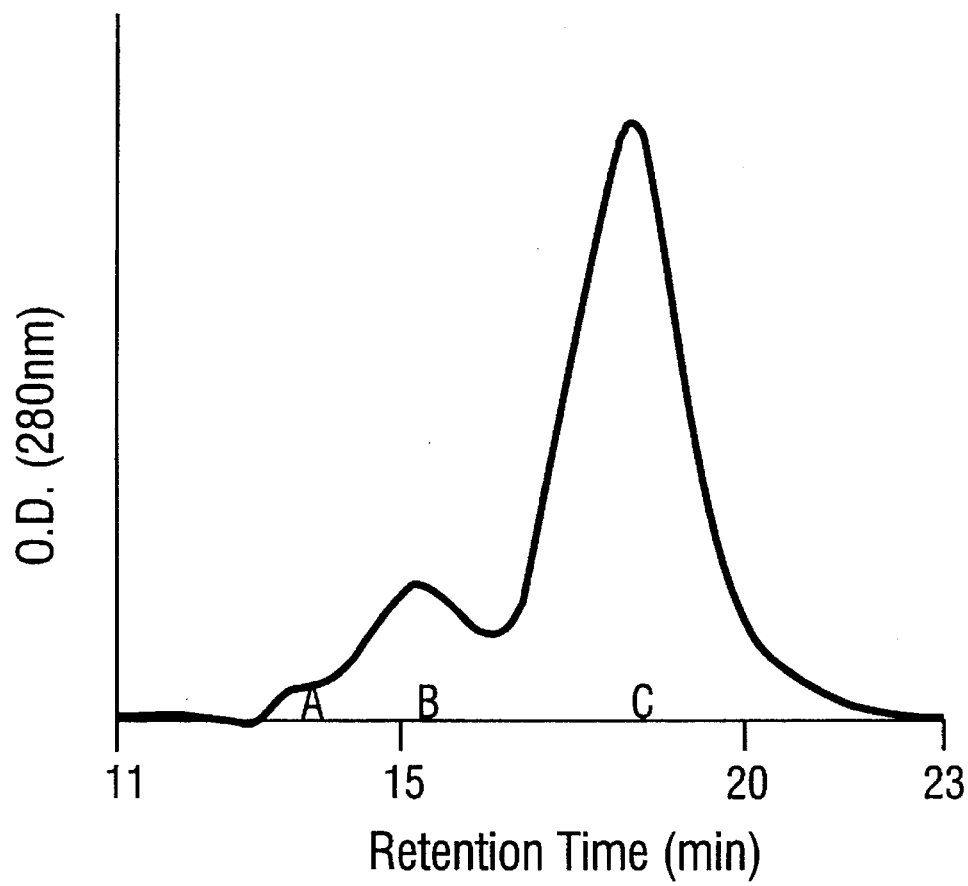

FIG. 2 is the HPLC on SEC-250 column of RFB4-SMPT-dgA. Peak A is MW>250 kDa (% of total=5%). Peak B is MW of 240 kDa (% of total=19%). Peak C is MW of 180–210 kDa (% of total=76%).

Figure 3:
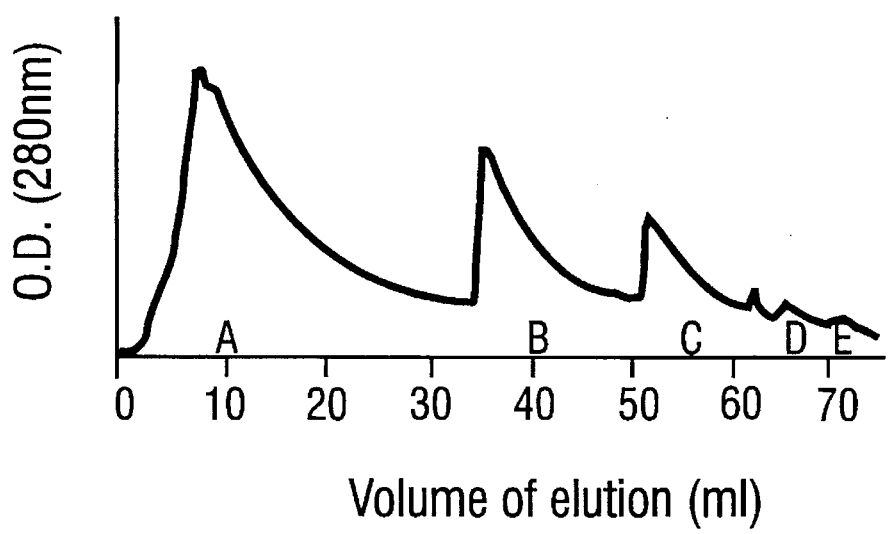

FIG. 3 is the rechromatography of RFB4-SMPT-dgA on Blue-Sepharose. Peak A is unbound IT. Peak B is bound and eluted with 0.1M NaCl. Peak C is bound and eluted with 0.2M NaCl. Peak D is bound and eluted with 0.3M NaCl. Peak E is bound and eluted with 0.5M NaCl.

Figure 4:
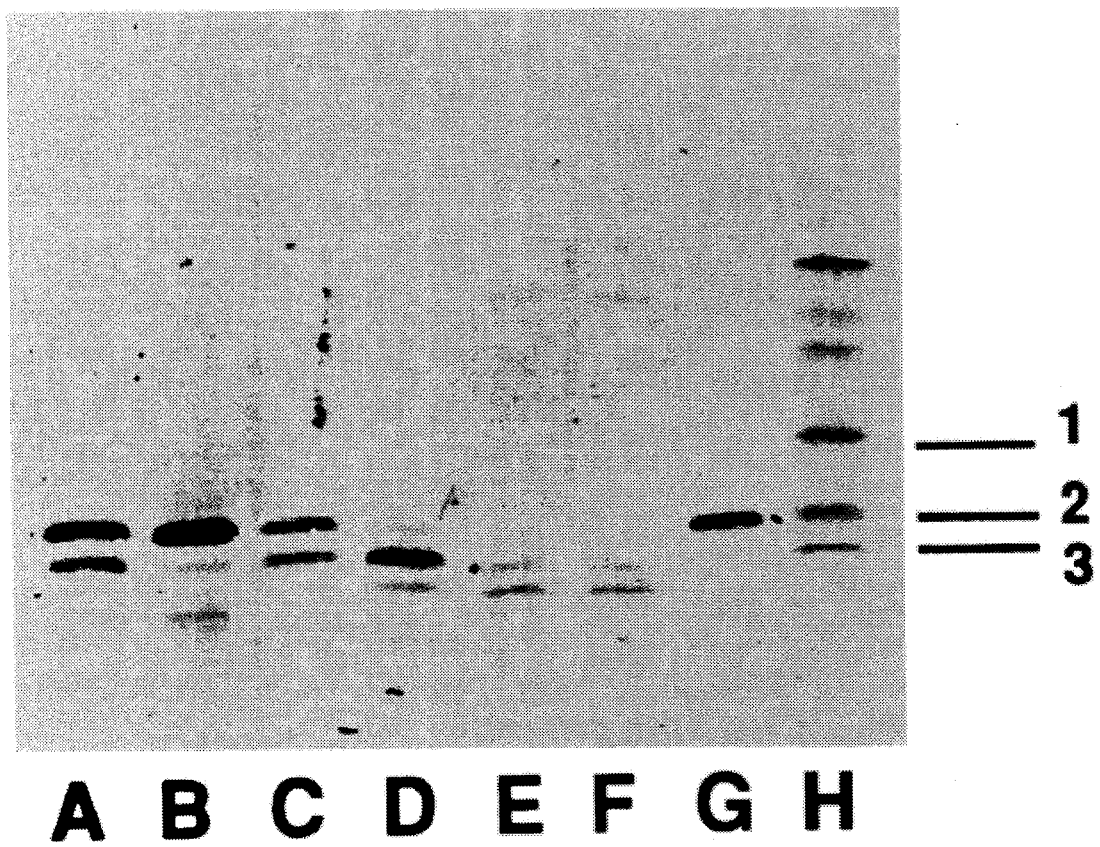

FIG. 4 is the SDS-PAGE of the RFB4-SMPT-dgA further purified by rechromatography on Blue-SEPHAROSE and gel filtration on Sephacryl S-300. FIG. 4 is a single gel which contains lanes A–H. Lane A is unpurified RFB4-SMPT-dgA. Lane B is the fraction unbound to Blue-SEPHAROSE in 0.05M PBE. Lane C is the fraction eluted with 0.1M NaCl. Lane D is the fraction eluted with 0.2M NaCl. Lane E is the fraction eluted with 0.3M NaCl. Lane F is the fraction eluted with 0.5M NaCl. Lane G is the second peak eluted from SEPHACRYL S-300. Lane H is high MW markers. The molecular weight markers are indicated as follows: 1 is 116 kDa; 2 is 170 kDa and 3 is 212 kDa.

Figure 5:
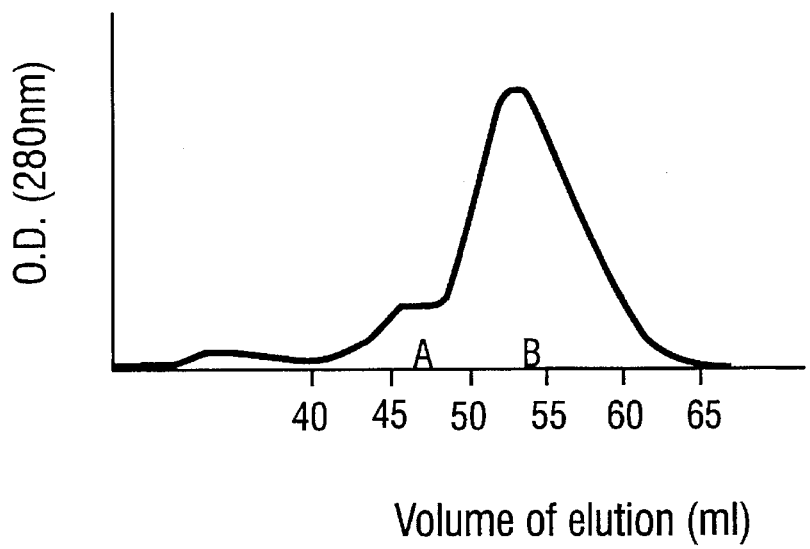

FIG. 5 is the gel filtration on SEPHACRYL S-300 of the fraction of RFB4-SMPT-dgA unbound to Blue-SEPHAROSE. Peak A is high MW IT (% of total=5%). Peak B is 180 kDa IT (% of total=95%).

Figure 6A:
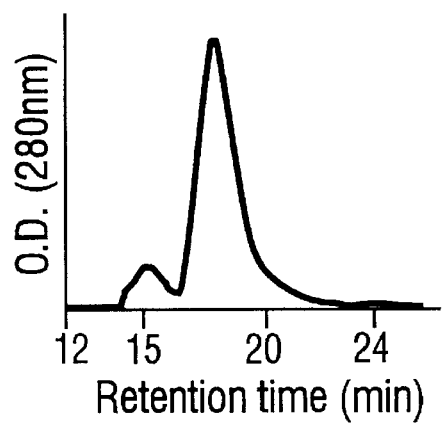

FIG. 6A: Fraction unbound to Blue-SEPHAROSE in 0.05M PBE after HPLC on SEC-250 of RFB4-SMPT-dgA further purified by rechromatography on Blue-SEPHAROSE and gel filtration on SEPHACRYL S-300.

Figure 6B:
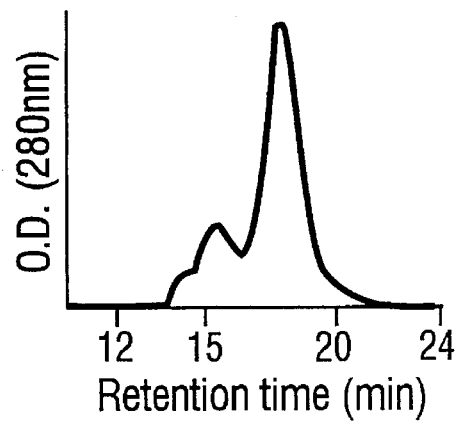

FIG. 6B: Fraction eluted with 0.2M NaCl from HPLC as in FIG. 6A.

Figure 6C:
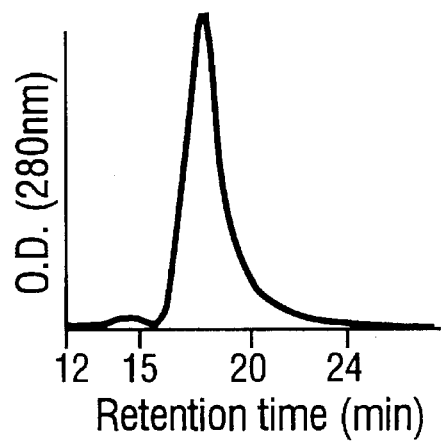

FIG. 6C: Second peak eluted from SEPHACRYL S-300 (180 kDa).

Figure 6D:
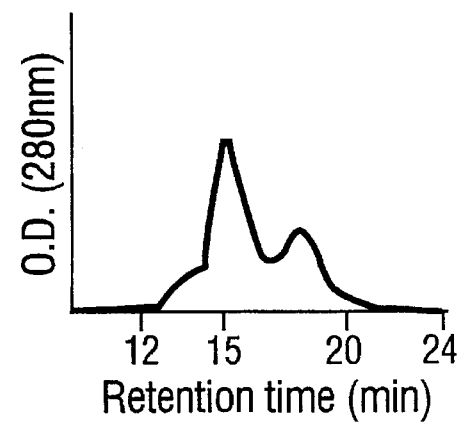

FIG. 6D: First peak eluted from SEPHACRYL S-300 (>250 kDa).

DETAILED DESCRIPTION OF THE PREFERRED EMBODIMENTS

Previous attempts to purify immunotoxins have resulted in a heterologous mixture of immunotoxins comprising one antibody molecule conjugated to one, two, three or possibly more toxin chains. In addition, larger, undefined species of immunotoxins which might comprise a single antibody molecule conjugated to more than three toxin chains, or which might comprise more than one antibody molecule were present in the mixture. These species of immunotoxins were difficult to separate because of their similarities in size and charge.

The present inventors made the surprising discovery that the heterologous mixture of immunotoxins, when rechromatographed, can be enriched for the individual species of immunotoxins. For example, immunotoxins of one, two or three toxin chains per molecule of antibody respectively, can be separated from each other by simple procedures. These new, homogenous immunotoxin preparations could then be evaluated to determine the most effective species to be used in therapeutic applications. This is an important step in immunotoxin therapy because the practitioner must balance the tumoricidal benefits with the side effects caused by nonspecific cytotoxicity and the patient's immune response to the immunotoxin. Having the homogenous immunotoxin preparations of the present invention available will aid greatly in the determination and administration of the most effective therapies.

Immunotoxins

Immunotoxins combine into a single molecule, the exquisite specificity of a ligand and the extraordinary toxicity of a toxin. Despite their conceptual simplicity, IT's are large and complex molecules that are continually undergoing improvements for optimal in vivo activity since each of their components—the binding moiety, the cross-linker, and the toxin, introduces a different set of problems that must be addressed for the IT to function optimally in vivo.

The targeting ligand of an IT is most often an antibody (Ab). The origin or derivation of the antibody or antibody fragment for use in the invention (e.g., Fab', Fab or F(ab')$_2$) is not crucial to the practice of the invention, so long as the antibody or fragment that is employed has the desired properties for the ultimately intended use of the IT. Thus, where monoclonal antibodies are employed, they may be of human, murine, monkey, rat, hamster, chicken or even rabbit origin. The invention also contemplates the use of human antibodies, "humanized" or chimeric antibodies from mouse, rat, or other species, bearing human constant and/or variable region domains, single chain antibodies, Fv domains, as well as recombinant antibodies and fragments thereof. Of course, due to the ease of preparation and ready availability of reagents, murine monoclonal antibodies will typically be preferred.

In certain therapeutic embodiments, one may use known antibodies, such as those having high selectivity for solid tumors, such as B72.3, PRBC5 or PR4D2 for colorectal tumors; HMFG-2, TAG 72, SM-3, or anti-p 185$^{Her2}$ for breast tumors; anti-p 185$^{Her2}$ for lung tumors; 9.2.27 for melanomas; and MO v18 and OV-TL3 for ovarian tumors. Anti-CD2 and anti-CD4 immunotoxins may be purified according to the invention and used to kill malignant T cells or HIV-infected cells. Also, CD3-specific immunotoxins may be purified and used to prevent acute graft-host disease after bone marrow transplantation.

In other embodiments, one may use another immunogen and prepare a new monoclonal antibody. The technique for preparing monoclonal antibodies is quite straightforward, and may be readily carried out using techniques well known to those of skill in the art, as exemplified by the technique of Kohler & Milstein (1975). Generally, immunogens are injected intraperitoneally into mice. This process is repeated three times at two-weekly intervals, the final immunization being by the intravenous route. Three days later the spleen cells are harvested and fused with SP2/0 myeloma cells by standard protocols (Kohler & Milstein, 1975): Hybridomas producing antibodies with the appropriate reactivity are then cloned by limiting dilution.

The toxins that have been used to form ITs are derived from bacteria or plants and are inhibitors of protein synthesis. They are among the most powerful cell poisons known. Fewer than ten molecules will kill a cell if they enter the cytosol (although many times that number must bind to the cell surface because the entry process is inefficient). This extraordinary potency initially led to the concern that such poisons were too powerful to control. However, the toxins can be rendered innocuous (except when directed to the target cells) simply by removing or modifying their cell-binding domain or subunit. The remaining portion of the toxin (lacking a cell-binding domain) is then coupled to a ligand (e.g., an antibody) that targets the toxic portion to the target cell. By selecting an antibody lacking unwanted cross-reactivity, ITs are safer and have fewer non-specific cytotoxic effects than most conventional anticancer drugs. The other main attraction of toxins is that because they are inhibitors of protein synthesis, they kill resting cells as efficiently as dividing cells. Hence, tumor or infected cells that are not in cycle at the time of treatment do not escape the cytotoxic effect of an IT.

"Toxin" is employed herein to mean any anticellular agent, and includes chemotherapeutic agents, radioisotopes as well as cytotoxins. In the case of chemotherapeutic agents, agents such as a hormone, asteroid for example; an antimetabolite such as cytosine arabinoside, fluorouracil, methotrexate or aminopterin; an anthracycline; mitomycin C; a vinca alkaloid; demecolcine; etoposide; mithramycin; or an antitumor alkylating agent such as chlorambucil or melphalan, may be used.

However, preferred toxins will be plant-, fungus- or bacteria-derived toxins, which, by way of example, include various A chain toxins, particularly ricin A chain, ribosome inactivating proteins such as saporin or gelonin, α-sarcin, aspergillin, restrictocin, ribonucleases such as placental ribonuclease, angiogenin, diphtheria toxin, and Pseudomonas exotoxin, to name just a few.

Plant toxins often contain two disulfide-bonded chains, the A and B chains. The B chain carries both a cell-binding region (whose receptor is uncharacterized) and a translocation region, which facilitates the insertion of the A chain through the membrane of a acid intracellular compartment into the cytosol. The A chain then kills the cell after incorporation. For their use in vivo, the ligand and toxin must be coupled in such a way as to remain stable while passing through the bloodstream and the tissues and yet be labile within the target cell so that the toxic portion can be released into the cytosol.

The most preferred toxin moiety for use in connection with the invention is ricin A chain, and particularly toxin A chain which has been treated to modify or remove carbohydrate residues, so-called deglycosylated A chain. Deglycosylated ricin A chain (dgA) is available commercially from Inland Laboratories, Austin, Tex.

However, it may be desirable from a pharmacologic standpoint to employ the smallest molecule possible that nevertheless provides an appropriate biological response. One may thus desire to employ smaller A chain peptides which will provide an adequate anti-cellular response. To this end, it has been discovered by others that ricin A chain may be "truncated" by the removal of 30 N-terminal amino acids by Nagarase (Sigma), and still retain an adequate toxin activity. It is proposed that where desired, this truncated A chain may be employed in conjugates in accordance with the invention.

Alternatively, one may find that the application of recombinant DNA technology to the toxin A chain moiety will provide additional significant benefits in accordance the invention. In that the cloning and expression of biologically active ricin A chain has now been enabled through the publications of others (O'Hare et al., 1987; Lamb et al., 1985; Halling et al., 1985), it is now possible to identify and prepare smaller or otherwise variant peptides which nevertheless exhibit an appropriate toxin activity. Moreover, the fact that ricin A chain has now been cloned allows the application of site-directed mutagenesis, through which one can readily prepare and screen for A chain derived peptides and obtain additional useful moieties for use in connection with the present invention.

The cross-linking of the toxin A chain region of the conjugate with the binding agent region is an important aspect of the invention. Where one desires a conjugate having biological activity, it is believed that a cross-linker which presents a disulfide function is required. The reason for this is unclear, but is likely due to a need for the toxin moiety to be readily releasable from the binding agent once the agent has "delivered" the toxin to the targeted cells. Each type of cross-linker, as well as how the cross-linking is performed, will tend to vary the pharmacodynamics of the resultant conjugate. Ultimately, one desires to have a conjugate that will remain intact under conditions found everywhere in the body except the intended site of action, at which point it is desirable that the conjugate have good "release" characteristics. Therefore, the particular cross-linking scheme, including in particular the particular cross-linking reagent used and the structures that are cross-linked, will be of some significance.

Cross-linking reagents are used to form molecular bridges that tie together functional groups of two different proteins (e.g., a toxin and a binding agent). To link two different proteins in a step-wise manner, heterobifunctional cross-linkers can be used which eliminate the unwanted homopolymer formation. An exemplary heterobifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the crosslinker, already tied up to the first protein, reacts with the cysteine residue (free sulfhydryl group) of the other protein (e.g., dgA).

The spacer arm between these two reactive groups of any cross-linkers may have various length and chemical composition. A longer spacer arm allows a better flexibility of the conjugate components while some particular components in the bridge (e.g., benzene group) may lend extra stability to the reactive group or an increased resistance of the chemical link to the action of various aspects (e.g., disulfide bond resistant to reducing agents).

The most preferred cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to its delivery to the site of action by the binding agent. The SMPT cross-linking reagent, as with many other known cross-linking reagents, lends the ability to crosslink functional groups such as the SH of cysteine or primary amines (e.g., the epsilon amino group of lysine). Another possible type of cross-linker includes the heterobifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

Although the "hindered" cross-linkers will generally be preferred in the practice of the invention, non-hindered linkers can be employed and advantages in accordance herewith nevertheless realized. Other useful cross-linkers, not considered to contain or generate a protected disulfide, include SATA, SPDP and 2-iminothiolane. The use of such cross-linkers is well understood in the art.

New Methods for Immunotoxin Preparation

Immunotoxins comprising monoclonal antibodies covalently bound to deglycosylated ricin A by hindered disulfide linkers have recently entered clinical trials for the treatment of non-Hodgkin's (B cell) lymphoma. These "second generation" immunotoxins are stable, long lived and display potent cytotoxicity to target cells. Standardized procedures for rapid preparation of high yields of these immunotoxins have been developed (Ghetie et al., 1991).

The procedure for preparation of the immunotoxins comprises the derivitization of antibodies with SMPT and reduction of deglycosylated ricin A (dgA) with dithiothreitol (DTT), followed by the reaction of the two components to establish a hindered interchain disulfide bond. The chemical crosslinking reaction results in a mixture of antibody, toxin and immunotoxins which are then purified, initially to remove the free antibody and free toxin molecules and subsequently to separate the different immunotoxin species which comprise one antibody molecule conjugated with one, two, three or more than three toxin molecules, respectively. The unreacted components of the crosslinking reaction may be removed by successive chromatographies on an affinity chromatography column such as activated dye/agarose to remove free antibody followed by gel filtration to remove high molecular weight material and free toxin.

The result of this procedure is a mixture of conjugates of various toxin/antibody ratios. An important embodiment of the present invention is the further purification of this mixture to obtain preparations essentially comprising immunotoxins of a single toxin/antibody ratio separated from immunotoxins of different toxin/antibody ratios. This purification is accomplished by further chromatographic separation which may be accomplished by affinity chromatography for example, using a salt gradient to elute the various species of immunotoxins and gel filtration to separate the immunotoxins from larger molecules.

Another important embodiment of the present invention is the ability to determine which of the dgA/IgG ratios is the most effective cytotoxic agent to be used in pharmacological preparations. For example, it was found that the unpurified mixture is more cytotoxic than the $dgA_1$/IgG preparation, and that the $dgA_2$/IgG is the most effective cytotoxic component of the preparation. The isolation and characterization of each of the single species of immunotoxin made possible by the present invention is of particular advantage in clinical applications as it allows the practitioner to exercise more precise control over the effective amount of immunotoxin to be administered in a particular situation. In addition, the purified immunotoxins, $dgA_1$/IgG and $dgA_2$/IgG are shown to be less toxic and less immunogenic than the nonpurified mixture and would therefore be expected to have less severe side effects in a patient.

Gel Filtration

A gel to be used in the procedures of the present invention is a three dimensional network which has a random structure. Molecular sieve gels comprise cross-linked polymers that do not bind or react with the material being analyzed or separated. For gel filtration purposes, the gel material is generally uncharged. The space within the gel is filled with liquid and the liquid phase constitutes the majority of the gel volume. Materials commonly used in gel filtration columns include dextran, agarose and polyacrylamide.

Dextran is a polysaccharide composed of glucose residues and is commercially available under the name SEPHADEX (Phamacia Fine Chemicals, Inc.). The beads are prepared with various degrees of cross-linking in order to separate different sized molecules by providing various pore sizes. Alkyl dextran is cross-linked with N,N'-methylenebisacrylamide to from SEPHACRYL-S300 which allows strong beads to be made that fractionate in larger ranges than SEPHADEX can achieve.

Polyacrylamide may also be used as a gel filtration medium. Polyacrylamide is a polymer of cross-linked acrylamide prepared with N,N'-methylenebisacrylamide as the cross-linking agent. polyacrylamide is available in a variety of pore sizes from Bio-Rad Laboratories (USA) to be used for separation of different size particles.

The gel material swell in water and in a few organic solvents. Swelling is the process by which the pores become filled with liquid to be used as eluant. As the smaller molecules enter the pores, their progress through the gel is retarded relative to the larger molecules which do not enter the pores. This is the basis of the separation. The beads are available in various degrees of fineness to be used in different applications. The coarser the bead, the faster the flow and the poorer the resolution. Superfine is to be used for maximum resolution, but the flow is very slow. Fine is used for preparative work in large columns which require a faster flow rate. The coarser grades are for large preparations in which resolution is less important than time, or for separation of molecules with a large difference in molecular weights. For a discussion of gel chromatography, see Freifelder, Physical Biochemistry, Second Edition, pages 238–246, incorporated herein by reference.

The most preferred methods of gel filtration for use in the present invention are those using dextran gels, such as SEPHADEX, and those using dextran-polyacrylamide gels such as SEPHACRYL which are able to separate molecules in the 180 to 240 kilodalton range.

Affinity Chromatography

Affinity chromatography is generally based on the recognition of a protein by a substance such as a ligand or an antibody. The column material may be synthesized by covalently coupling a binding molecule, such as an activated dye, for example to an insoluble matrix. The column material is then allowed to adsorb the desired substance from solution. Next, the conditions are changed to those under which binding does not occur and the substrate is eluted. The requirements for successful affinity chromatography are that the matrix must adsorb molecules, the ligand must be coupled without altering its binding activity, a ligand must be chosen whose binding is sufficiently tight, and it must be possible to elute the substance without destroying it.

A preferred embodiment of the present invention is an affinity chromatography method wherein the matrix is a reactive dye-agarose matrix. Blue-SEPHAROSE, a column matrix composed of Cibacron Blue 3GA and agarose or SEPHAROSE may be used as the affinity chromatography matrix. The most preferred matrix is SEPHAROSE CL-6B available as Reactive Blue 2 from Sigma Chemical Company, catalogue #R 8752. This matrix binds the immunotoxins of the present invention directly and allows their separation by elution with a salt gradient.

Pharmaceutical Preparations

Pharmaceutical aqueous compositions of the present invention comprise an effective amount of the IT dissolved or dispersed in a pharmaceutically acceptable carrier or aqueous medium. The phrases "pharmaceutically or pharmacologically acceptable" refers to molecular entities and compositions that do not produce an adverse, allergic or other untoward reaction when administered to a human. As used herein, "pharmaceutically acceptable carrier" includes any and all solvents, dispersion media, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The following buffers and reagents are particularly contemplated for use in the preparation of pharmaceutical preparations of the present invention: dgA, deglycosylated ricin A chain; DMF, dimethylformamide (Pierce, Rockford, Ill.); DTT (Pierce); PBE, 0.05M sodium phosphate, pH 7.5 with 1 mM EDTA; PBES, 0.05M sodium phosphate, pH 7.5 with various concentrations of NaCl (such as 0.1M, 0.2M, 0.3M, 0.4M and 0.5M NaCl) and 1 mM EDTA; PBSE, 0.01M sodium phosphate, pH 7.5 with 0.17M NaCl and 1 mM EDTA; SMPT, N-succinimidyl-oxycarbonyl-$\alpha$-methyl-$\alpha$(2-pyridyldithio)toluene (Pierce). All buffers may be prepared with endotoxin-free distilled water using enzyme grade salts (Fisher Biotec, Springfield, N.J.).

The ITs may be formulated for parenteral administration, e.g., formulated for injection via the intravenous, intramuscular or sub-cutaneous routes. The preparation of an aqueous composition that contains an IT as an active ingredient will be known to those of skill in the art in light of the present disclosure, as exemplified by Remington's Pharmaceutical Sciences, 16th Ed. Mack Publishing Company, 1980, incorporated herein by reference. Moreover, for human administration, it will be understood that preparations should meet sterility, pyrogenicity, general safety and purity standards as required by FDA Office of Biological Standards.

Typically, such compositions can be prepared as injectables, either as liquid solutions or suspensions; solid forms suitable for using to prepare solutions or suspensions upon the addition of a liquid prior to injection can also be prepared; and the preparations can also be emulsified. The compositions will be sterile, be fluid to the extent that easy syringability exists, stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

Although it is most preferred that solutions of ITs be prepared in sterile water containing other non-active ingredients, made suitable for injection, solutions of ITs can also be prepared in water suitably mixed with a surfactant, such as hydroxypropylcellulose, if desired. Dispersions can also be prepared in liquid polyethylene glycols, and mixtures thereof and in oils. The carrier can also be a solvent or dispersion medium containing, for example, water, ethanol, polyol (for example, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Upon formulation, solutions will be administered in a manner compatible with the dosage formulation and in such amount as is therapeutically effective. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

It is particularly contemplated that suitable pharmaceutical IT compositions will generally comprise from about 10 to about 100 mg of the desired IT conjugate admixed with an acceptable pharmaceutical diluent or excipient, such as a sterile aqueous solution, to give a final concentration of about 0.25 to about 2.5 mg/ml with respect to the conjugate, in, for example, 0.15M NaCl aqueous solution at pH 7.5 to 9.0. The preparations may be stored frozen at $-10°$ C. to $-70°$ C. for at least 1 year.

ELISA

ELISAs may be used in conjunction with the invention. In an ELISA assay, proteins or peptides incorporating dgA antigen sequences are immobilized onto a selected surface, preferably a surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of milk powder. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/TWEEN. These added agents also tend to assist in the reduction of nonspecific background. The layered antisera is then allowed to incubate for from 2 to 4 hours, at temperatures preferably on the order of $25°$ to $27°$ C. Following incubation, the antisera-contacted surface is washed so as to remove non-immunocomplexed material. A preferred washing procedure includes washing with a solution such as PBS/TWEEN, or borate buffer.

Following formation of specific immunocomplexes between the test sample and the bound antigen, and subsequent washing, the occurrence and even amount of immunocomplex formation may be determined by subjecting same to a second antibody having specificity for the first. To provide a detecting means, the second antibody will preferably have an associated enzyme that will generate a color development upon incubating with an appropriate chromogenic substrate. Thus, for example, one will desire to contact and incubate the antisera-bound surface with a urease or peroxidase-conjugated anti-human IgG for a period of time and under conditions which favor the development of immunocomplex formation (e.g., incubation for 2 hours at room temperature in a PBS-containing solution such as PBS-Tween).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline-6-sulfonic acid [ABTS] and $H_2O_2$, in the case of peroxidase as the enzyme label. Quantification is then achieved by measuring the degree of color generation, e.g., using a visible spectra spectrophotometer.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

Preparation of Immunotoxins

The IT containing deglycosylated RTA (dgA) and a murine $IgG_1$ monoclonal directed against the human CD22 molecule (RFB4) was prepared (RFB4-SMPT-dgA) and purified as reported below (Ghetie et al., 1991). The IT was stored at −70° C.

Buffers and reagents

The following buffers and reagents were used: dgA, deglycosylated ricin A chain; DMF, dimethylformamide (Pierce, Rockford, Ill.); DTT (Pierce); PBE, 0.05M sodium phosphate, pH 7.5 with 1 mM EDTA; PBES, 0.05M sodium phosphate, pH 7.5 with various concentrations of NaCl (such as 0.1M, 0.2M, 0.3M, 0.4M and 0.5M NaCl) and 1 mM EDTA; PBSE, 0.01M sodium phosphate, pH 7.5 with 0.17M NaCl and 1 mM EDTA; SMPT, N-succinimidyl-oxycarbonyl-α-methyl-α(2-pyridyldithio)toluene (Pierce). All buffers were prepared with endotoxin-free distilled water using enzyme grade salts (Fisher Biotec, Springfield, N.J.).

Antibodies

Hybridoma cells secreting mouse IgG1 anti-CD22 (RFB4) were obtained from Dr. G. Janossy (London, U.K.). Hybridoma cells secreting mouse IgG1 antiCD19 (HD37) can be obtained from Dr. G. Moldenhauer and Dr. B. D örken (Heidelberg, F. R. G.), if desired. 10–20 g batches of purified antibodies from these hybridoma cells were produced by Abbott Laboratories (Needham Heights, Mass.) and contained less than 5% impurities as determined by sodium dodecylsulfate-polyacrylamide gel electrophoresis (SDS-PAGE) and low levels of endotoxin (2 EU/ml). The proteins were supplied in 0.01M phosphate buffered saline, pH 7.2 and were stored at −70° C. Protein concentrations were calculated from the optical density of the solution using an absorption coefficient of 1.4 (1 mg/ml, 1 cm, 280 nm).

Deglycosylated ricin A chain (dgA)

The dgA was purchased from Inland Laboratories, Austin, Tex., and was prepared and characterized as described (Fulton et al., 1986). The protein was dissolved in phosphate buffered saline, pH 7.2 containing 50% glycerol and was stored at −20° C. The protein contained less than 0.1 U of endotoxin per 3 mg/ml. Protein concentrations were calculated from the optical density of the solution using an absorption coefficient of 0.77 (1 mg/ml, 1 cm, 280 nm).

Preparation of immunotoxins

All procedures were performed in good laboratory practice (GLP) laboratory using a chromatographic system described in (Ghetie, et al., 1988a; 1991). The buffers were maintained in sterile square barrels at 4° C. and pumped directly into the chromatographic system. All columns and gels were purchased from Pharmacia (Piscataway, N.J.). The preparation required 2–3 days and the purification was performed in 2 days. Provided that the system did not require cleaning with 0.1M NaOH (e.g. to remove endotoxin or adsorbed protein) four batches of immunotoxin could be prepared per month, each yielding 1.5 g from 6.0 g of antibody and 3.0 g of dgA. This is enough to treat approximately 85–90 patients at the MTD.

RFB4-SMPT-dgA; Preferred Method of Preparation

Six grams of RFB4 antibody dissolved in 800 ml of 0.01M phosphate buffered saline, pH 7.2 were adjusted to pH 7.5 with 10N NaOH. The protein solution was then mixed with 1/50 of its volume of SMPT (5 mg/ml DMF) giving a final concentration of 0.1 mg SMPT/ml which is equivalent to 5.0-fold molar excess over the antibody. The mixture was then stirred gently under $N_2$ for 1 h at room temperature and applied to a Sephadex G-25M column (25×60 cm) equilibrated with $N_2$-flushed PBE. The protein eluate containing RFB4-MPT was collected and concentrated to 1.5 liter (approximately 4 mg/ml) using the Amicon CH2 ultrafiltration unit at 2°–8° C. Samples were removed for the determination of the average number of MPT groups per molecule of IgG using the method of Carlson et al. (1978). The pH of the dgA solution (3 mg/ml) was adjusted to 7.5 with 10N NaOH and 3 g of this solution was then mixed with 1/10 its volume of DTT (7.7 mg/ml) in PBE and stirred in the dark for 1 h at room temperature. The mixture (approximately 1 liter) was then applied to a SEPHADEX G-25M column (25×60 cm) in $N_2$-flushed PBE. The reduced dgA was collected and concentrated to 750 ml (approximately 4 mg/ml) and immediately mixed with SMPT-derivatized antibody solution (1500 ml at 4 mg/ml). The reaction mixture was sterilized by filtration through a 0.22 μm membrane and was maintained at room temperature for 2 days. Samples were removed for SDS-PAGE and LAL testing. The reaction mixture was applied to a 11.6×30 cm column of Blue-SEPHAROSE CL-6B equilibrated with PBE. After washing to remove unbound protein (nonreacted antibody) the immunotoxin and free dgA were collected by elution with PBES. The protein solution was concentrated to 1.5 liter and filtrated through a SEPHACRYL S-200HR column (25×90 cm) equilibrated with 0.15M NaCl, containing 5 mM lysine. The first major peak containing the immunotoxin was concentrated to 0.5 mg/ml, sterilized through a 0.22 μm filter and distributed into vials of appropriate capacity.

RFB4-SMPT-dgA; Alternative Method of Preparation

Six grams of RFB4 antibody dissolved in 500 ml of 0.01M phosphate buffered saline, pH 7.2 were applied to a SEPHACRYL S200-HR column (25 cm diameter×90 cm length) equilibrated in BSE at 2°–8° C. The 150 kDa (monomer) peak was collected and concentrated to 7.5 mg/ml in an Amicon CH2 ultrafiltration unit at 2°–8° C. The protein solution was then mixed with 1/50 of its volume of SMPT (Pierce) (4.5 mg/ml DMF) giving a final SMPT concentration of 0.09 mg/ml which is equivalent to a 4.7-fold molar excess over the antibody. The mixture (containing 5.5 g of IgG in 700 ml) was then stirred gently under $N_2$ for 1 h at room temperature and applied to a SEPHADEX G-25M column (25×60 cm) equilibrated in N$_2$-flushed PBSE. The protein eluate (containing MPT antibody free of unreacted SMPT) was collected and concentrated as indicated above to approximately 2 liters (2.5 mg/ml). Samples were removed for SDS-PAGE and LAL testing and for the determination of the average number of MPT groups per molecule of IgG using the method of Carlson et al. (1978). The pH of the dgA solution was adjusted to 7.5 with 10N NaOH. Three grams of dgA were then mixed with 0.1 vol. of DTT (7.7 mg/ml PBSE) and stirred in the dark for 1 h at room temperature. The mixture (approximately 1 liter) was then applied to a SEPHADEX G25M column (25×60 cm) in N$_2$-flushed PBSE. The DTT-free, reduced dgA was collected and samples were removed for SDS-PAGE and LAL testing. The dgA solution (approximately 3 liters) was mixed with the SMPT-derivatized antibody (2 liters) and the mixture was concentrated to 5 mg/ml (total protein) at 2°–8° C. (approximately 1.8 liter, final volume). The reaction mixture was sterilized by filtration through a 0.22 µm membrane (Nalgene disposable filterware, Nalge Company, Rochester, N.Y.) and maintained at room temperature under N$_2$ for 3 days. Samples were removed for SDS-PAGE and LAL testing.

The reaction mixture was mixed with 1/100 of its volume of cysteine (free base) (2.5 mg/ml) in PBSE. After stirring for 6 h at room temperature, the mixture was filtered through a 0.8 µm filter to remove any particulate matter and the solution was applied to a SEPHACRYL S-200HR column (25×90 cm) in BE at 28°–8° C. The peaks with molecular masses between 150 and 210 kDa were collected. This semi-purified immunotoxin (containing free IgG) was concentrated to approximately 1.5 mg/ml (total protein) and samples were removed for SDS-PAGE and LAL testing. Unreacted RFB4 antibody was removed by affinity chromatography on a 11.6×30 cm Blue -SEPHAROSE CL-6B column (capacity 3 g dgA) equilibrated with BE. The column was washed with this buffer until all unbound antibodies were removed and then the purified RFB4-SMPT-dgA was displaced from the column with BES. The protein solution was dialyzed by diafiltration in an Amicon CH2 unit into 0.15M NaCl containing 5 mM lysine at 2°–8° C. using approximately 10–15 liters of lysine-containing saline. The protein concentration was adjusted to 0.5 mg/ml using an absorption coefficient of 1.3 (for 1 mg/ml, 1 cm, 280 nm). Finally, the immunotoxin was sterilized through a 0.22 µm filter and distributed into vials.

Analysis of the immunotoxins

All assays except the measurement of antibody activity have been described by Ghetie et al., (1988a), incorporated herein by reference. To measure antibody activity, samples of Daudi cell suspension (10$^6$ cells/0.1 ml) were treated with various concentrations of immunotoxin or unconjugated antibody (from 0.05 to 5 nM) and after a 15 min incubation at 4° C. the cells were washed twice with phosphate buffered saline containing 0.02% sodium azide. Cells were then treated with 3 µl of fluorescent goat antimouse Ig (Kirkegaard and Perry Labs, Gaithersburg, Md.) per 50 µl cells suspension containing 10$^6$ cells. After another 15 minutes of incubation at 4° C. the cells were washed once and suspended in 0.5 ml 1% paraformaldehyde in phosphate buffered saline with sodium azide and the percentage of fluorescent cells determined by FACS. The percentage of fluorescent cells vs. protein concentration in nM was plotted and the protein concentration staining 50% of treated cells was determined. The relative antibody activity of the immunotoxin was calculated as a percentage of the initial antibody activity with the equation:

$$100 \times \frac{[Ab]}{[immunotoxin]} = \text{relative antibody activity}$$

where [Ab] and [immunotoxin] are the concentrations of antibody and immunotoxin staining half of the treated cells.

Cleaning the chromatographic system

When endotoxin contamination of the chromatographic system occurred, columns were 'cleaned' before use by incubation with 0.1M NaOH for 48–72 h at 2°–8° C. as described (Ghetie et al., 1988a).

EXAMPLE II

Purification of Immunotoxins

Methods

The cell free rabbit reticulocyte assay and the Daudi cell killing assay have been described (Press et al., 1988; Ghetie et al., 1988b; each incorporated herein by reference). SDS-PAGE was carried out using the Pharmacia Phast System with a 4–15% gel gradient and low and high MW standards. The LD$_{50}$ was determined in groups of four BALB/c mice injected intraperitoneally with different doses of the IT. The primary antibody response against dgA was determined in groups of 3 mice injected i.p. with 5 µg/g animal of ITs. The animals were bled two weeks after injection. The antibody titer was estimated using an ELISA (Amlot et al., 1993). The half-life was determined in mice injected with $^{125}$I-labeled ITs as previously described (Fulton et al., 1988).

High performance liquid chromatography (HPLC) was performed on 7.5×600 mm SEC-250 analytical columns (Bio-Rad, Hercules, Calif.). The retention times of various peaks were compared to those of standard proteins of known MWs. Gel filtration on SEPHACRYL S-300 was performed on 15×600 mm columns equilibrated with phosphate buffered saline. Chromatography on Blue-SEPHAROSE was performed in 30 ml packed gel columns, equilibrated in 0.05M phosphate buffer with 0.003M Na$_2$EDTA, pH 7.5 (PBE). A stepwise gradient comprising 0.1M, 0.2M, 0.3M and 0.5M NaCl dissolved in PBE was applied to elute the bound protein.

Results

Figure 1:
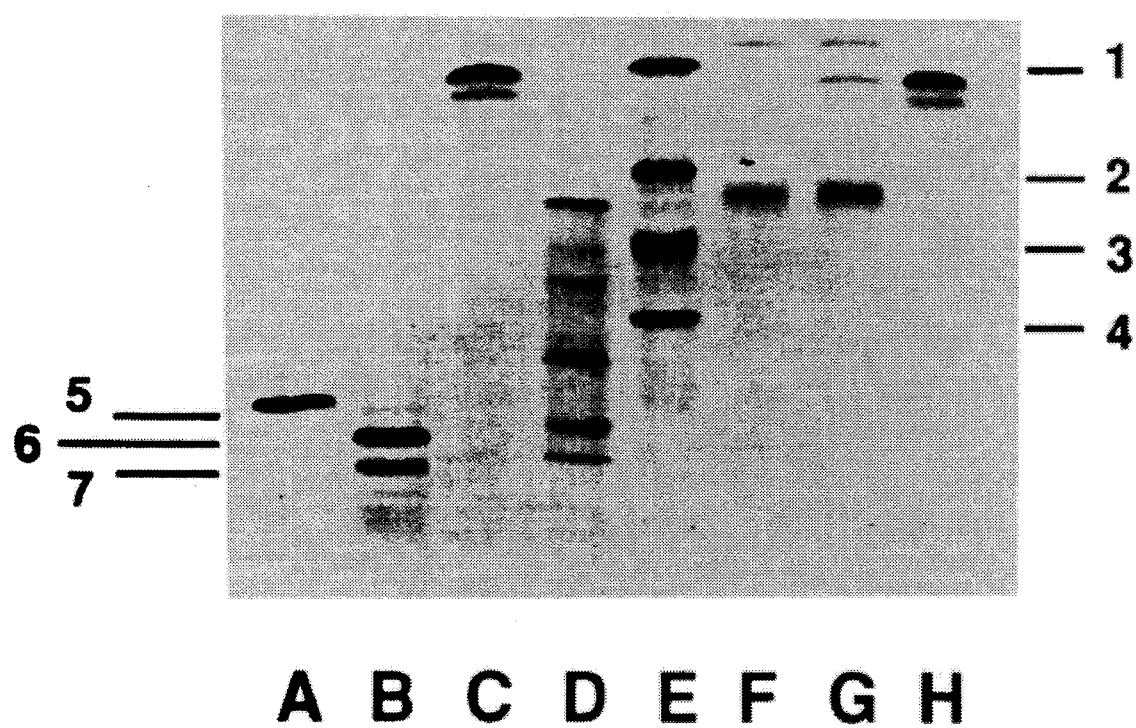
FIG. 1 is the SDS-PAGE of RFB4-SMPT-dgA.

RFB4-SMPT-dgA has been described previously and is currently being used in clinical trials (Amlot et al., 1993). This IT was submitted to SDS-PAGE and HPLC. The results presented in FIGS. 1 and 2 demonstrate that the preparation is heterologous and comprises several molecular species with molecular weights (MWs) ranging between 180 KDa and>250 kDa. The major chromatographic peak (76%) has a MW ranging between 180–210 kDa and includes a mixture of two ITs, containing one and two molecules of dgA linked to one molecule of IgG$_1$. The second peak (19%) has a MW of 240 kDa and is thought to comprise three molecules of dgA linked to one molecule of antibody. The first peak (5%) has a MW>250 kDa and may contain a mixture of conjugates with dgA/IgG$_1$ molar ratios of 4 or greater. When this material was analyzed on SDS-PAGE five bands were observed. The first three had MWs corresponding to molecules of dgA/IgG$_1$ with molar ratios of 1, 2 and 3. The two faint bands had MWs in a range that could not be determined on this gel. The apparent discrepancy between the results of HPLC and SDS-PAGE is due to the fact that the SEC-250 column does not allow separation of the 180 kDa and 210 kDa ITs while these two ITs are completely separated by SDS-PAGE.

Pure immunotoxin preparations were obtained by an additional chromatography step. The heterologous mixture was chromatographed on Blue-SEPHAROSE. A NaCl gradient was used to separate the conjugates comprising different molar ratios of dgA/IgG$_1$ (FIG. 3). Unexpectedly, 50% of the protein applied to the Blue-SEPHAROSE column did not bind, despite the fact that the same buffer (PBE) had been used to purify the original IT (Ghetie et al., 1991). Hence, 50% of the IT had lost its ability to interact a second time with Blue-SEPHAROSE. When this material was analyzed by SDS-PAGE and HPLC, it contained only the first band (or the third peak) (MW-180 kDa) and a small amount (10%) of the fourth and fifth bands (or the first peak) (MW>250 kDa) (FIGS. 4 and 6D). The difference in the MW of these species facilitated complete separation of the 180 kDa IT from the heavier MW ITs by gel filtration on SEPHACRYL S-300 (FIG. 5). The second major peak contained only the 180 kDa IT as shown in FIG. 6C.

After collecting the non-bound fraction, a stepwise gradient was used to elute material from the Blue-SEPHAROSE column. Four fractions were collected by eluting the column with 0.1M, 0.2M, 0.3M and 0.5M NaCl. The 0.1M fraction contained a small percentage of 180 kDa IT and the bulk of the 210 kDa IT, while the 0.2M fraction contained the 210 kDa IT almost exclusively. The 0.3M and 0.5M fractions contained equal proportions of 210 kDa IT and>250 kDa IT (FIG. 4; Lanes C, D, E and F).

The unpurified RFB4-SMPT-dgA IT also contains a small amount of higher MW components. The exact MW of these two heavy MW ITs (bands 4 and 5 in SDS-PAGE and peak 1 in HPLC) cannot be determined accurately by these procedures, but they are>250 kDa. It is, therefore, possible that these ITs contain 4 or more dgA molecules per molecule of antibody, but it is also possible that antibody dimerization occurred and these conjugates contain two molecules of dimerized antibody linked to an undetermined number of dgA molecules. This latter possibility is favored by the fact that the heavy MW ITs are not bound to Blue-SEPHAROSE in 0.05M PBE pH 7.5, a behavior quite unexpected for a conjugate having 4 or more dgA molecules bound to one molecule of antibody.

It is unclear why half of the initial IT eluted from Blue-SEPHAROSE during the first purification did not bind to the Blue-SEPHAROSE during the second passage. The lack of binding is not due to freezing or to the high salt concentration since similar results were obtained using freshly prepared IT and an IT obtained by elution in 0.15M NaCl. The dgA in the unbound fraction (containing mainly dgA$_1$/IgG) had the same enzymatic activity as the dgA in the fraction eluted at 0.2M (containing the dgA$_2$/IgG conjugate) as shown in Table 1. Therefore, the lower activity of the dgA$_1$/IgG vs dgA$_2$/IgG was not due to partial inactivation of the dgA moiety in the IT containing one dgA molecule. The fact that the initial IT preparation is more active than that with one dgA molecule (1.3 vs 2.6×10$^{-12}$M) is not a consequence of a partial inhibition of the dgA activity in the dgA$_1$/IgG conjugate, but results from the fact that the initial IT contained 30% dgA$_2$/IgG (which is 7 times more active than dgA$_1$/IgG).

EXAMPLE III

Biological Activity of Purified Immunotoxins

The biological activity of the purified 180 kDa IT was tested and compared with that of the initial preparation of IT (containing all 5 electrophoretic bands) and that of the fraction eluted with 0.2M NaCl, containing mainly the 210 kDa IT (two molecules of dgA linked to one molecule of antibody, dgA$_2$/IgG). The results are presented in Table 1.

The results indicate that the ability of the different species of IT to inhibit protein synthesis in a cell free system is not dependent on the dgA/IgG$_1$ molar ratio since all three preparations had comparable activity. In contrast, when the different ITs were tested for their ability to specifically kill Daudi cells, in vitro, the IT containing two molecules of dgA per molecule of antibody was 7 times more cytotoxic than the IT with one dgA molecule per molecule of antibody. The latter was 2-fold less active than the unpurified IT preparation. Preliminary studies presented in Table 1 also indicate that the unpurified IT is more toxic than the purified 180 kDa and 210 kDa components and that the primary antibody response against the unpurified IT is higher than for the purified 180 kDa and 210 kDa preparations. This suggests that it may be possible to decrease both toxicity and immunogenicity of the ITs by further purification. The halflife of the IT containing two molecules of dgA was significantly shorter than that of the IT with one dgA molecule, indicating that the latter will persist longer in the circulation of tumor-bearing individuals.

The present results indicate that target cell killing is increased about 7 fold when a conjugate containing two molecules of dgA is used compared to a conjugate containing one molecule of dgA. This finding suggests that the former IT may have an increased therapeutic index in vivo. The immunogenicity of the two appear similar. Since the half-life of the two ITs are not the same, it will be of considerable importance to determine if there is a significant advantage of one molecular species over another in tumor therapy studies in mice.

TABLE 1

| | The biological activity of purified and unpurified RFB4-SMPT-dgA | | |
|---|---|---|---|
| Biological Activity | Starting Material | Purified 180 kDa component | Purified 210 kDa component |
| Inhibition of cell free protein synthesis (IC50, M) | 4.0 × 10$^{-11}$ | 3.0 × 10$^{-11}$ | 4.1 × 10$^{-11}$ |
| Cytotoxicity to Daudi cells (IC50, M)[a] | 1.3 ± 0.2 × 10$^{-12}$ | 2.6 ± 0.35 × 10$^{-12}$ | 0.4 ± 0.04 × 10$^{-12}$ |
| Half-life in | 27.5 ± 3.0 | 32.0 ± 3.5 | 19.2 ± 0.6 |

TABLE 1-continued

The biological activity of purified and unpurified RFB4-SMPT-dgA

| Biological Activity | Starting Material | Purified 180 kDa component | Purified 210 kDa component |
|---|---|---|---|
| mice (hrs)[b] | | | |
| Toxicity to mice[c] (LD50, ug/g animal) | 6.2 | 10.0 | 9.2 |
| Anti-dgA titer in mice (ug/ml)[d] | 3.9 | 2.5 | 2.6 |

[a] $P < 0.01$ for the difference in activity between the 180 kDa and 210 kDa components (mean of 5 experiments)
[b] 3 mice/group
[c] 4 mice/group
[d] 3 mice/group

EXAMPLE IV

Clinical Use of Immunotoxins

The present example is provided to outline the use of ITs for the treatment of lymphoma, and is just one example of the many uses in which ITs prepared in accordance with the invention may be employed.

Patients

To be eligible for treatment, patients should preferably be over 18 years of age with histologically confirmed, relapsing non-Hodgkin's lymphoma (NHL); a Karnofsky performance status of ±30% and a life expectancy of ±2 months; ±15% of their lymphoma cells should express CD22 antigen at ±10% of its density on a Daudi B cell line; and they would have clinically or radiologically measurable disease. Patients would have generally relapsed following at least one course of conventional therapy and most have been intensively treated with combination chemotherapy (100%), radiotherapy (56%) and autologous bone marrow transplantation (19%). Conventional therapy should be stopped at least 2 weeks before treatment except for corticosteriods which may be maintained at their previous dosage throughout.

Patients would be excluded from the study if they had CNS disease, severe infection, autoimmune vasculitis, inflammatory arthritis, cardiac, renal (creatinine ±170 μM) or hepatic dysfunction (bilirubin ±25 μM), allergy or antibodies to mouse immunoglobulin (M1 g) or dgA.

Immunophenotyping of the lymphoma

Blood, bone marrow (BM) and/or lymph node (LN) biopsies would be obtained from each patient. Lymphoid cells would be separated from blood and BM using Lymphoprep and mechanically teased from lymph nodes. The lymphoid cells would be stained for a variety of T and B cell antigens (CD2, CD3, CD4, CD5, CD6, CD10, CD19, CD20, CD21, CD22 [RFB4], CD37 and immunoglobulin [κ, λ, μ, δ, γ, and α chains], and were assessed for the intensity of CD22 (RFB4) antigen expression (compared to Daudi cells) by flow cytometry. Lymphoma cells and Daudi cells would be stained in parallel with an irrelevant IgGlk (MOPC-21) and RFB4, followed by FITC-goat anti-mouse Ig.

Immunotoxin administration

RFB4-SMPT-dgA would be prepared as described herein. For intravenous access, an indwelling subclavian catheter would be inserted before starting treatment. The immunotoxin would be filtered through a 0.22 um filter and infused over 4 hours in 100 ml of saline; one would preferably administer 4 infusions of immunotoxin 48 hours apart. The rationale of this approach is to give all the immunotoxin before any host antibody response against the immunotoxin (usually by 10–14 days following xenogenic immunoglobulin) could occur.

Two patients could be treated at each total dose level and dosages could start at 5% of the mouse $LD_{50}$ rising to 10%, 15% and so on until grade III or IV toxicity was encountered in any patient. The total dose could be achieved by intrapatient escalation of RFB4-SMPT-dgA doubling with each successive dose. Thus at 10%LD50 successive doses of 0.67%, 1.33%, 2.67% and 5.33% LD50 would be given representing 1/15, 2/15, 4/15 and 8/15 of the planned total dose. Patients could also receive the planned total dose as 4 equally divided doses. Patients could receive between 2 and 12 infusions. The number of infusions would, of course, be dependent upon the grade of any toxicity produced by previous infusions. The LD50 would be taken as the standard for biological activity of different Lots of immunotoxin and if the LD50 does not differ between the Lots, dosage would be expressed as mg/m2.

Patient examination

Before entry into the study patients would undergo a physical examination, measurement of vital signs, respiratory function tests, EKG, chest X-rays, MUGA scans, CT scans of chest, abdomen and pelvis. Laboratory measurements would include full blood counts, lymphoma phenotyping, examination of CSF, PT, PTT, fibrinogen levels, serum creatinine, creatine kinase, electrolytes, urea, AST, ALT, bilirubin, albumin, total serum protein and immunoglobulins. Physical examination, EKG and laboratory tests would be performed daily during immunotoxin administration until 2 days after the last dose and then weekly thereafter. Serum samples would be taken weekly after the immunotoxin treatment for evaluation of human anti-mouse (HAMA) and anti-ricin (HARA) responses until patients came off study.

Grading of toxicity

Adverse effects would be graded as Grade I (mild), II (moderate), III (severe) or IV (life threatening) based on WHO guidelines with modifications as appropriate. If patients experience Grade I or lower toxicity, they would complete a scheduled four doses of immunotoxin and could have a further four doses thereafter if (i) the tumor burden was reduced by at least 50% and (ii) there was no HAMA or HARA. After Grade II toxicity further doses could be delayed for 24 hours to allow improvement. At Grade III toxicity administration of immunotoxin would be stopped until improvement had occurred and doses could then be continued at half the previous level. Grade 4 toxicity would be an absolute contraindication to further immunotoxin therapy.

Pharmacokinetics

The assays used to determine immunotoxin levels in the blood are well known. Serum samples would be obtained at 0, 1, 3, 4, 8, 12, 24 and 48 hours after each infusion. Half-lives and other pharmacokinetic parameters would be analyzed using the PKCALC program (1987) developed by Dr. R. C. Shumaker, Merrel Dow Research Institute, Cincinnati, Ohio. Pharmacokinetic analysis would be performed on every infusion with a sufficient series of detectable immunotoxin levels.

Evaluation of tumor responses

Clinical responses would be scored using WHO criteria to define partial (PR) and complete responses (CR) by linear measurement of masses detectable clinically and by CT scanning. Evaluation of linearly, unmeasurable disease such as BM infiltration, leukemic cells and ill-defined tissue infiltration would not be undertaken unless evaluating a possible CR in which case all previously involved sites would have to be proven free of disease by biopsy. Physical examination would be performed weekly after treatment and CT scans would be carried out between 2–7 days and again at one month after treatment. Patients would come off study when their disease progressed and/or they were treated with chemotherapy, radiotherapy or an increased dose of corticosteroids. Patients with large tumors (L: 10 cm in maximum diameter or 100 cm total measurable area) would be distinguished from those with smaller masses (S: 10 cm and 100 cm ).

Statistical analysis

Statistical analysis may be performed using the SPSS statistical package, for example. SPSS Inc. Illinois, USA and Student's T-test. ANOVA. Mann-Whitney U-test and Pearson product moment correlation techniques may be used depending on whether continuous, categorical, multiple or skewed distribution variables are being analyzed.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Amlot, P. L., Stone, M. J., Cunningham, D., Fay, J., Newman, J., Collins, R., May, R. D., McCarthy, M., Richardson, J., Ghetie, V., Ramilo, O., Thorpe, P. E., Uhr, J. W. and Vitetta, E. S. (1993) Blood, In press, 1993.

Freifelder, D. 1982, physical Biochemistry, Second Edition, W. H. Freeman and Company, San Francisco.

Fulton, R. J., Blakey, D. C., Knowles, P. P., Uhr, J. W., Thorpe, P. E. and Vitetta, E. S. (1986) J. Biol. Chem. 261, 5314.

Fulton, R. J., Tucker, T. F., Vitetta, E. S. and Uhr, J. W. (1988) Cancer Res. 48, 2618.

Ghetie, V., Ghetie, M-A., Uhr, J. W. and Vitetta, E. S. (1988a) J. Immunol. Methods 112, 267.

Ghetie, M. A., May, R. D., Till, M., Uhr, J. W., Ghetie, V., Vitetta, E. S., Knowles, P. P., Relf, M., Braun, A. M., Wallace, P. M., Thorpe, P. E., Amlot, P. and Janossy, G. (1988b) Cancer Res 48, 2610.

Ghetie, V., Thorpe, P. E., Ghetie, M-A., Knowles, P., Uhr, J. W. and Vitetta, E. S. (1991) J Immunol Methods 142, 223.

Halling et al. (1985) Nucl. Acids Res., 13, 8019.

Kohler & Milstein (1975) Nature, 256,495.

Lamb et al. (1985) Eur. J. Biochem., 148, 265.

Lord, J. M., Spooner, R. A., Hussar, K. and Roberts, L. M. (1988) Adv. Drug Delivery Rev. 2, 297.

Marsh, J. W. and Neville, D. M., Jr. (1986) Biochemistry 25, 4461.

Masuho, Y., Kishida, K., Saito, M., Umeto, N. and Hara, T. (1982) J. Biochem. 91, 1583.

O'Hare et al. (1987) FEBS Lett., 210,731.

Press, O. W., Martin, P., Thorpe, P. E. and Vitetta, E. S. (1988) J. Immunol. 141, 4410.

Remington's Pharmaceutical Sciences, 16th Ed. Mack Publishing Company, 1980

What is claimed is:

1. An immunotoxin preparation comprising a substantially purified immunotoxin species, wherein said immunotoxin species is an antibody molecule conjugated to two plant toxin A chains of the same kind and lacking a cell binding B chain, said immunotoxin species being more than about 50% by weight of the total immunotoxin present in the preparation.

2. The immunotoxin preparation of claim 1, wherein said antibody molecule is a monoclonal antibody.

3. The immunotoxin preparation of claim 1, wherein said monoclonal antibody is a mouse monoclonal antibody.

4. The immunotoxin preparation of claim 1, wherein said toxin chain is deglycosylated ricin A.

5. The immunotoxin preparation of claim 1 wherein said immunotoxin species is from greater than about 50% to about 92% by weight of the total immunotoxin in said preparation.

6. The immunotoxin preparation of claim 5 wherein said immunotoxin species is more than about 70% by weight of the total immunotoxin.

7. The immunotoxin preparation of claim 6 wherein said immunotoxin species is about 92% by weight of the total immunotoxin.

8. Antibodies conjugated to plant toxin A chains of the same kind that lack a cell binding B chain, wherein more than about 50% by weight of said antibodies are conjugated to two such toxins of the same kind.

* * * * *